(12) United States Patent
Yamashita et al.

(10) Patent No.: US 12,264,395 B2
(45) Date of Patent: Apr. 1, 2025

(54) SURFACE-MODIFIED MAGNESIUM ALLOY

(71) Applicant: Japan Medical Device Technology Co., Ltd., Kumamoto (JP)

(72) Inventors: Shuzo Yamashita, Kumamoto (JP); Makoto Sasaki, Kumamoto (JP); Akira Wada, Kumamoto (JP)

(73) Assignee: Japan Medical Device Technology Co., Ltd., Kumamoto (JP)

( * ) Notice: Subject to any disclaimer, the term of this patent is extended or adjusted under 35 U.S.C. 154(b) by 681 days.

(21) Appl. No.: 17/486,372

(22) Filed: Sep. 27, 2021

(65) Prior Publication Data
US 2022/0033974 A1 Feb. 3, 2022

Related U.S. Application Data

(63) Continuation of application No. PCT/JP2020/013769, filed on Mar. 26, 2020.

(30) Foreign Application Priority Data

Mar. 28, 2019 (JP) ................................ 2019-062875
Jan. 8, 2020 (JP) ................................ 2020-001521

(51) Int. Cl.
*C23C 28/04* (2006.01)
*A61L 31/02* (2006.01)
*C22C 23/04* (2006.01)
*C23C 16/26* (2006.01)

(52) U.S. Cl.
CPC ............ *C23C 28/04* (2013.01); *A61L 31/024* (2013.01); *C22C 23/04* (2013.01); *C23C 16/26* (2013.01)

(58) Field of Classification Search
CPC . C22C 23/00; C22C 23/04; C22F 1/06; C23C 16/26; C23C 28/04; A61L 31/024
See application file for complete search history.

(56) References Cited

U.S. PATENT DOCUMENTS

| | | | |
|---|---|---|---|
| 8,435,287 B2 | 5/2013 | Nakatani et al. | |
| 9,402,669 B2 | 8/2016 | Neubert et al. | |
| 2019/0330718 A1 | 10/2019 | Ueda et al. | |
| 2019/0343666 A1 | 11/2019 | Sasaki et al. | |
| 2020/0001013 A1 | 1/2020 | Holmqvist | |
| 2021/0115539 A1 | 4/2021 | Jeda et al. | |
| 2021/0353836 A1 | 11/2021 | Yamashita et al. | |

FOREIGN PATENT DOCUMENTS

| | | | |
|---|---|---|---|
| CN | 101370448 A | 2/2009 | |
| CN | 105177500 A | 12/2015 | |
| EP | 3950989 A1 | 2/2022 | |
| JP | 2007195883 A | 8/2007 | |
| JP | 2014533967 A | 12/2014 | |
| JP | 2017094016 A | 6/2017 | |
| WO | WO-2017035072 A1 * | 3/2017 | .......... A61L 31/022 |
| WO | 2018131476 A1 | 7/2018 | |
| WO | 2018139647 A1 | 8/2018 | |
| WO | 2019182003 A1 | 9/2019 | |
| WO | 2020012529 A1 | 1/2020 | |
| WO | 2020158761 A1 | 8/2020 | |

OTHER PUBLICATIONS

Cabrini, M. C. P. L. S. P. T., et al. "Evaluation of corrosion resistance of biocompatible coatings on magnesium." La Metallurgia Italiana (2014).*
Poinern, G. Eddy Jai, Sridevi Brundavanam, and Derek Fawcett. "Biomedical magnesium alloys: a review of material properties, surface modifications and potential as a biodegradable orthopaedic implant." American Journal of Biomedical Engineering 2.6 (2012): 218-240.*
Chinese Office Action for Chinese Application No. 202080025409.2, mailed Feb. 11, 2022, (16 pages).
Kun, "China magnesium industry progress," Metallurgical Industry Press, pp. 127-131, 2012, (14 pages). (English Translation).
International Preliminary Report on Patentability for International Application No. PCT/JP2020/013769, mailed Oct. 7, 2021, (11 pages).
Extended European Search Report for European Application No. 20778706.0 mailed Mar. 15, 2023, (7 pages).
Indian Office Action, and English Translation thereof, for Indian Application No. 202117045938, mailed Dec. 7, 2022, (9 pages).
International Search Report, and English Translation thereof, for International Application No. PCT/JP2020/013769, mailed May 12, 2020, (6 pages).
Zhang et al., "Characterization and degradation comparison of DLC film on different magnesium alloys", Journal of Surfaces & Coatings Technology, vol. 205, No. Supplement 1, pp. 515-520, 2010, (6 pages).
Wei et al., "Corrosion resistance and surface biocompatibility of diamond-like carbon coating on AZ31D magnesium alloy", International Journal of Surface Science and Engineering, vol. 10, No. 2, pp. 101-115, 2016, (15 pages).
JP Patent Search Machine Translation for JP2014533967A.
English Abstract for WO2018139647A1. Espacenet.
English Abstract for WO2018131476A1. Espacenet.
English Abstract for WO2019182003A1. Espacenet.
English Abstract for WO2020012529A1. Espacenet.

(Continued)

*Primary Examiner* — Jessee R Roe
(74) *Attorney, Agent, or Firm* — Kagan Binder, PLLC

(57) ABSTRACT

To provide a magnesium alloy with improved corrosion resistance by surface modification, and a production method thereof. (1) The surface-modified magnesium alloy comprising: a magnesium alloy having an arbitrary shape; a magnesium fluoride layer formed by fluorination of the surface of the magnesium alloy; and a diamond-like carbon layer formed on the magnesium fluoride layer. (2) The method comprising: subjecting a surface of a magnesium alloy having an arbitrary shape to fluorination treatment to form a magnesium fluoride layer on the surface of the magnesium alloy, and then subjecting the magnesium alloy with the magnesium fluoride layer to be placed in a high-frequency plasma CVD device such that a source gas containing carbon is introduced to form a diamond-like carbon layer on the magnesium fluoride layer.

7 Claims, 2 Drawing Sheets

(56) References Cited

OTHER PUBLICATIONS

Espacenet English Abstract for and JP Patent Search Machine Translation for JP2017195883A.
Espacenet English Abstract for and JP Patent Search Machine Translation for JP2017094016A.
Notice of Reasons for Refusal, mailed in JP Application No. 2021-509606, mailed on Aug. 8, 2023, 10 pages (Official Copy & English Translation).

* cited by examiner

SURFACE-MODIFIED MAGNESIUM ALLOY

CROSS REFERENCE TO THE RELATED APPLICATION

This application is a continuation application, under 35 U.S.C § 111(a) of international application No. PCT/JP2020/013769, filed Mar. 26, 2020, which claims priority to Japanese patent applications No. 2019-062875 filed Mar. 28, 2019 and No. 2020-001521 filed Jan. 8, 2020, the entire disclosures of which are herein incorporated by reference as a part of this application.

FIELD OF THE INVENTION

The present invention relates to a surface-modified magnesium alloy (also referred to as a coating-modified magnesium alloy) in which the surface of the biodegradable magnesium alloy is protected by coating the surface thereof with a corrosion inhibiting layer. The surface-modified magnesium alloy according to the present invention is used as implants and the like for orthopedic surgery, oral surgery, plastic surgery, cardiovascular surgery, or cerebral surgery.

BACKGROUND OF THE INVENTION

In modern medical technology, implants are widely applied as supports for surgical purposes, such as for attachment or fixation of tissue or bones. However, the implants remaining in the human body after given treatment would induce various complications in the human body. Accordingly, there is an inconvenience such that the inserted implant must be removed from the human body through additional treatment after achieving the purpose of the implant.

Many studies have been done to produce implants from biodegradable materials as implant metals, and as a result, biodegradable materials consisting of a variety of materials such as polymer-based materials, ceramic-based materials, and metal-based materials have been proposed.

In response to this, the development of metal materials having biodegradability as well as strength, processability and ductility has been eagerly desired, and magnesium, iron, tungsten, and the like have been proposed as biodegradable materials. Of these materials, magnesium has been particularly attracting attention as the most suitable biodegradable material, and recently, magnesium alloys have begun to be used for some fixing screws and the like for bonding bones.

The rate of biodegradation of biodegradable materials in vivo must proceed in proportion to the rate of tissue regeneration. Where the degradation rate of the magnesium alloy is too fast, the magnesium alloy would lose stability before recovery of the damaged tissues, resulting in failure of basic function as the medical instrument. On the contrary, if the degradation rate of the magnesium alloy is too slow, it would result in higher risk such as complication. Therefore, the control of the degradation rate of biodegradable magnesium corresponds to an essential factor to be considered in the design of medical instruments using biodegradable magnesium. Therefore, as a surface treatment of the biodegradable magnesium alloy, an attempt has been made to treat the surface of the magnesium alloy by fluorination (Patent Document 1, etc.).

CONVENTIONAL ART DOCUMENT

Patent Document

[Patent Document 1] WO 2018/139647

SUMMARY OF THE INVENTION

Problems to be Solved by the Invention

The present inventors have found that, in order to appropriately control the degradation rate of the surface of the magnesium alloy, it is not sufficient just to form a magnesium fluoride layer on the surface of the magnesium alloy by treating the surface of the magnesium alloy with hydrofluoric acid as described in the above-mentioned conventional art document.

Therefore, the problem to be solved by the present invention is to obtain a surface-modified magnesium alloy that can be used as the material of implants by forming a magnesium fluoride layer on the surface of the magnesium alloy, and further a corrosion-resistant layer on the magnesium fluoride layer to suppress the degradation rate of the magnesium alloy. As a result of intensive studies on the above problems, the inventors of the present invention have reached the present invention.

Means to Solve Problems

The present invention may include the following aspects.
Aspect 1
A surface-modified magnesium alloy comprising: a magnesium alloy having an arbitrary shape; a magnesium fluoride layer formed by fluorination of a surface of the magnesium alloy; and a diamond-like carbon layer formed on the magnesium fluoride layer.

The present inventors have found that degradation rate of the surface of the magnesium alloy can be appropriately controlled by forming a magnesium fluoride layer (first layer) on the surface of the magnesium alloy by means of giving fluorinated treatment on the surface of the magnesium alloy, and further forming a diamond-like carbon layer (second layer) on the magnesium fluoride layer, whereby a practical implant for medical use can be obtained.

The magnesium alloys preferably include AZ series (Mg—Al—Zn) (AZ31, AZ61, AZ91 and the like), AM series (Mg—Al—Mn), AE series (Mg—Al—RE), EZ series (Mg—RE-Zn), ZK series (Mg—Zn—Zr), WE series (Mg—RE-Zr), AX or AXJ series (Mg—Al—Ca), etc. Among them, preferable one may include a magnesium alloy which contains 90 mass % or more of magnesium, and zinc (Zn), zirconium (Zr), and manganese (Mn) as accessory components, and does not contain aluminum and rare earth metals that are harmful to the human body.

By using the magnesium alloy, the surface of the magnesium alloy is fluorinated to form a fluorinated layer, and further, a diamond-like carbon layer is formed on the fluorinated layer, whereby the biodegradation rate of the magnesium can be controlled within a suitable range for implants. Each of the fluorinated layer and the diamond-like carbon layer is preferably formed over the entire surface of the magnesium alloy.

Aspect 2
The surface-modified magnesium alloy according to aspect 1, wherein the magnesium alloy contains, in % by mass, 0.95 to 2.00% Zn, 0.05% or more and less than 0.30% Zr, 0.05 to 0.20% Mn, and the balance consisting of Mg and unavoidable impurities, with an average crystal grain size of 1.0 to 3.0 μm and a standard deviation of grain size distribution of 0.7 or less.

Since the magnesium alloy constituting the surface-modified magnesium alloy is used for the treatment of the human body and may be indwelled in the human body for a certain period of time, from the viewpoint of safety to the human body, this magnesium alloy preferably contains, in % by mass, 0.95 to 2.00% Zn, 0.05% or more and less than 0.30% Zr, 0.05 to 0.20% Mn, and the balance consisting of Mg and unavoidable impurities, with an average crystal grain size of 1.0 to 3.0 μm and a standard deviation of grain size distribution of 0.7 or less. Among them, the magnesium alloy which has a total amount of unavoidable impurities of 30 ppm or less and is free from rare earth elements and aluminum is preferable.

The above magnesium alloy may have a fracture elongation of 15 to 50% as measured in accordance with JIS Z2241. The fracture elongation preferably exceeds 30%.

The magnesium alloy may have a tensile strength of 250 to 300 MPa and a proof stress of 145 to 220 MPa as measured in accordance with JIS Z2241.

The magnesium alloy is preferably free from precipitates having a grain size of 500 nm or larger, and more preferably free from precipitates having a grain size of 100 nm or larger.

Aspect 3

The surface-modified magnesium alloy according to aspect 1 or 2, wherein the magnesium alloy has a wheel shape, a plate shape, a rod shape, a pipe shape, a band shape, a wire shape, a ring shape, or a combination of at least one shape as described above, and such a shape is selected in accordance with an intended purpose for the magnesium alloy.

Aspect 4

The surface-modified magnesium alloy according to any one of aspects 1 to 3, wherein the surface-modified magnesium alloy is an alloy for orthopedic implants, an alloy for oral surgery implants, an alloy for plastic surgery implants, an alloy for cardiovascular surgery implants, or an alloy for cerebral surgery implants.

Aspect 5

The surface-modified magnesium alloy according to any one of aspects 1 to 4, wherein the surface-modified magnesium alloy is an alloy used for suture instruments such as clips, staplers, wires, and surgical needles, and for bone junction members such as bone pins, bone screws and suture anchors, or for therapeutic implants such as gastrointestinal and esophageal implants, or other therapeutic implants such as circulatory stents, lower extremity stents, and aneurysm coils.

Therapeutic implants used as gastrointestinal and esophageal implants, and circulatory stents, lower extremity stents, and aneurysm coils can be collectively referred to as implants for the luminal region, while implants for suture instruments and bone junction members can be collectively referred to as implants for the non-luminal region.

Aspect 6

The surface-modified magnesium alloy according to any one of aspects 1 to 5, wherein the magnesium fluoride layer has a layer thickness of 0.5 to 1.5 μm.

Although a magnesium fluoride layer formed on the surface of the magnesium alloy is effective in reducing the degradation rate of the magnesium alloy, it may be difficult to form a magnesium fluoride layer at a thickness exceeding 1.5 μm by means of hydrofluoric acid treatment. Accordingly, the thickness of the magnesium fluoride layer may be appropriately selected from the range of 0.5 to 1.5 μm.

Aspect 7

The surface-modified magnesium alloy according to any one of aspects 1 to 6, wherein the diamond-like carbon layer has a layer thickness of 10 nm to 5 μm.

According to the present invention, since a diamond-like carbon layer is formed on the magnesium fluoride layer, it is possible to control the degradation rate of the magnesium alloy effectively even where the diamond-like carbon layer has a thin thickness.

Aspect 8

The surface-modified magnesium alloy according to any one of aspects 1 to 7, wherein the diamond-like carbon layer is a silicon-containing diamond-like carbon layer.

Aspect 9

The surface-modified magnesium alloy according to any one of aspects 1 to 8, wherein a biodegradable polymer layer is formed on at least a part of the surface of the diamond-like carbon layer.

Aspect 10

A method of producing a surface-modified magnesium alloy comprising (1) a magnesium fluoride layer on a surface of a magnesium alloy and (2) a diamond-like carbon layer on the magnesium fluoride layer, the method comprising:

(1) subjecting a surface of a magnesium alloy having an arbitrary shape to fluorination treatment to form a magnesium fluoride layer on the surface of the magnesium alloy, and then (2) subjecting the magnesium alloy with the magnesium fluoride layer to be placed in a high-frequency plasma CVD device such that a source gas (such as acetylene, methane) containing carbon is introduced to form a diamond-like carbon layer on the magnesium fluoride layer.

As mentioned above, the magnesium alloy may have a wheel shape, a plate shape, a rod shape, a pipe shape, a band shape, a wire shape, a ring shape, or a combination of at least one shape as described above. That is, the magnesium alloy may have various shapes depending on use. The variously shaped magnesium alloy is immersed into hydrofluoric acid solution so as to perform a fluorination treatment, and then, the magnesium alloy with the magnesium fluorinated layer is placed in a CVD device, and a source gas (raw material gas) containing carbon is introduced to form the diamond-like carbon layer on the magnesium fluorinated layer. As a result, a surface-modified magnesium alloy according to the present invention can be produced.

Aspect 11

The aspect 11 according to the present invention relates to a method according to aspect 10, that is, a method of producing a surface-modified magnesium alloy, wherein as the source gas containing carbon, a source gas further containing silicon (such as monomethyl silane, triethyl silane, tetramethyl silane) is used to form a silicon-containing diamond-like carbon layer on the magnesium fluoride layer.

Note that any combination of at least two components disclosed in the claims and/or the drawings is included in the present invention. In particular, any combination of two or more of the following claims is included in the present invention.

Effects of the Invention

According to the first aspect of the present invention, the surface-modified magnesium alloy enables to have a corrosion resistance, as well as to maintain the mechanical strength for a predetermined period of time, in which the surface-modified magnesium alloy is obtained by forming a magnesium fluoride layer on the surface of a magnesium alloy and then forming a carbon-coating layer of diamond-like carbon on the magnesium fluoride layer.

Since the diamond-like carbon layer is further formed on the magnesium fluoride layer, is provided a surface-modified magnesium alloy having sufficient corrosion resistance for various applications.

The magnesium fluoride layer is biodegraded and absorbed into the body, but the diamond-like carbon layer is not absorbed into the body. By forming the diamond-like carbon layer on the magnesium fluoride layer, it is possible to make the diamond-like carbon layer thinner, and as a result, the influence of the remaining diamond-like carbon layer in the body can be reduced.

According to the second aspect of the present invention, the magnesium alloy free from rare earth metals and aluminum is excellent in safeness to human bodies. The magnesium alloy may include an alloy composed of substantially single-phase solid solution or has a microstructure in which nanometer-sized fine Zr-bearing precipitates are dispersed in the single-phase alloy. The magnesium alloy has excellent deformability (ductility, elongation ability) because of its fine and uniform particle size and has excellent mechanical properties such as tensile strength and proof strength because of the absence of coarse precipitates at which a fracture starts.

The magnesium alloy may have each of the unavoidable impurities of Fe, Ni, Co, and/or Cu at a content of lower than 10 ppm. The magnesium alloy may preferably be free of Co as an unavoidable impurity.

The surface-modified magnesium alloy comprising the above magnesium alloy may have excellent deformation characteristics and biodegradation characteristics of which are adequately controlled.

In the third aspect of the present invention, since both the first layer and the second layer formed on the surface of the magnesium alloy with an arbitrary shape have excellent deformation followability, the surface-modified magnesium alloy can be used for various purposes.

In the fourth and fifth aspects of the present invention, the surface-modified magnesium alloy according to the present invention can be used for various therapeutic applications, and eventually, the magnesium alloy itself is decomposed and absorbed into the body tissue, while the diamond-like carbon layer is closely attached to the surface of the body tissue and buried therein thanks to thin thickness.

In the sixth and seventh aspects of the present invention, the thickness of the magnesium fluoride layer and the diamond-like carbon layer should be considered in a balance between the deformation followability of the magnesium fluoride layer and the deformation followability (generation of cracks) of the diamond-like carbon layer, although the corrosion resistance improves as the thickness increases.

In the eighth aspect of the present invention, where a diamond-like carbon layer containing silicon is selected as the diamond-like carbon layer, the effect of suppressing the decomposition rate of magnesium is enhanced, compared to a magnesium alloy comprising a diamond-like carbon layer without silicon. The inclusion of silicon also suppresses the delamination of the diamond-like carbon layer after an implant with the diamond-like carbon layer is inserted into the body.

In the ninth aspect of the present invention, it is preferred that a biodegradable polymer layer is formed on at least a part of the surface of the diamond-like carbon layer. The biodegradable polymer layer facilitates smooth insertion of the surface-modified magnesium alloy product into a predetermined part of a living body, and the biodegradable polymer layer can contain a drug (such as a limus-based vascular intimal thickening inhibiter).

The biodegradable polymer may comprise two layers, an inner layer on the diamond-like carbon layer side, and an outer layer on the living body side; and the drug may be contained in the inner layer, the outer layer, or both.

According to the tenth and eleventh aspects of the present invention, a magnesium fluoride layer (first layer) is formed on the surface magnesium alloys having various shapes, and a diamond-like carbon layer (second layer) is further formed on the magnesium fluoride layer (first layer). Accordingly, a surface-modified magnesium alloy having a first layer and a second layer can be produced.

BRIEF EXPLANATION OF THE DRAWINGS

The present invention will be more clearly understood from the preferred embodiments described below with reference to the attached drawings. However, the embodiments and the drawings are merely illustrative and explanatory, and should not be used for defining the scope according to the present invention. The scope according to the present invention is defined by the attached claims.

DESCRIPTION OF THE EMBODIMENTS

Surface-Modified Magnesium Alloy

Figure 1:
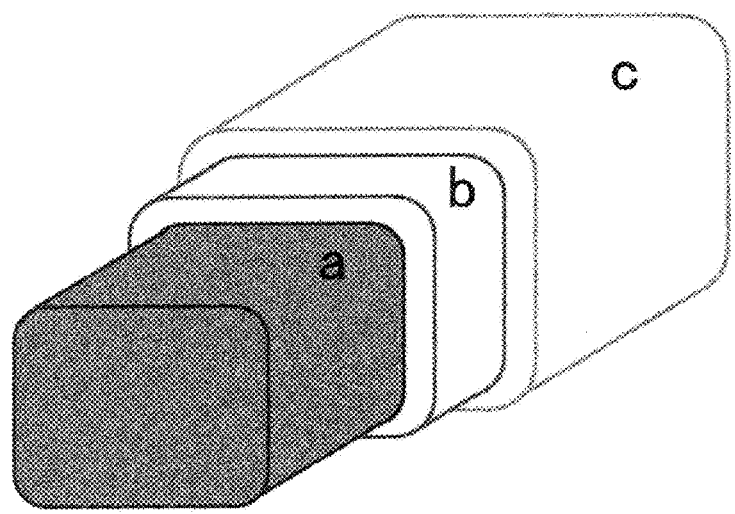
FIG. 1 is a schematic view illustrating components of a surface-modified magnesium alloy according to an embodiment of the present invention.

An example of the surface-modified magnesium alloy (Mg alloy) according to the present invention comprises, as shown in FIG. 1, a magnesium alloy (a) having a predetermined shape, a magnesium fluoride ($MgF_2$) layer (first layer) (b) on the surface of the magnesium alloy via fluorination [the surface exhibits hydrophilicity due to inclusion of $Mg(OH)_2$ and the like formed by oxidation of Mg on the surface], and a diamond-like carbon layer (second layer) (c) are formed on the magnesium fluoride layer (b)

The technical elements of the above configuration include: an element to select a magnesium alloy composition that is biodegradable and adaptable to an application; an element to form a magnesium fluoride layer (first layer) containing $MgF_2$ as a main component on the magnesium alloy surface to control corrosion of the magnesium alloy having the selected alloy composition; and an element to form a carbon-coating layer (second layer) comprising a diamond-like carbon on the surface of the magnesium fluoride layer.

Magnesium Alloy

Magnesium Alloys used in the present invention may include AZ series (Mg—Al—Zn) (AZ31, AZ61, AZ91 and the like), AM series (Mg—Al—Mn), AE series (Mg—Al—RE), EZ series (Mg—RE-Zn), ZK series (Mg—Zn—Zr), WE series (Mg—RE-Zr), AX or AXJ series (Mg—Al—Ca), etc. Moreover, examples thereof may include a magnesium alloy which contains 90 mass % or more of magnesium, and zinc (Zn), zirconium (Zr), and manganese (Mn) as accessory components, and does not contain aluminum and rare earth metals (RE) that are harmful to the human body. According to the present invention, the surface-modified magnesium alloy may preferably contain 90 mass % or more of magnesium (Mg) as a main component, zinc (Zn), zirconium (Zr) and manganese (Mn) as accessory components, and 30 ppm or less of unavoidable impurities selected from the group consisting of iron (Fe), nickel (Ni), cobalt (Co), and copper (Cu), and excluding aluminum and at least one sort of rare earths selected from the group consisting of scandium (Sc), yttrium (Y), dysprosium (Dy), samarium (Sm), cerium (Ce), gadolinium (Gd), and lanthanum (La). This specific composition secures safety to living body as well as mechanical properties.

From the viewpoint of enhancing safety to living body and mechanical property, the content of Mg is preferably 93 mass % or more, and still more preferably 95 mass % or more.

By not containing at least one sort of rare earths selected from the group consisting of Sc, Y, Dy, Sm, Ce, Gd, and La, and aluminum (Al), it is possible to prevent harm to the human body.

The preferred magnesium alloy according to the present invention includes, in % by mass, 0.95 to 2.00% of zinc, equal to or higher than 0.05% and less than 0.30% of zirconium, 0.05 to 0.20% of manganese, and the balance consisting of magnesium and unavoidable impurities, with an average crystal grain size of 1.0 to 3.0 μm and a standard deviation of grain size distribution of 0.7 or less.

According to the present invention, benefit such as improvement in plastic workability can be achieved by controlling the composition of the magnesium alloy within the above range. Further, the characteristics such as fracture elongation are improved by refining/uniformizing the particle size of the alloy.

The magnesium alloy having the above composition can avoid formation of coarse precipitates which may be triggers (starting points) of fractures and thereby reduce the possibility of breakage during and after deformation. It should be noted that although Zr, which is added in order to reduce the crystal particle size of the alloy, may form precipitates, the precipitates are typically dispersed at a nanometer scale (in a size smaller than 100 nm) in the matrix phase and thus has a negligible impact on deformation and corrosion of the alloy.

Zinc (Zn): In % by Mass, 0.95% or More and 2.00% or Less

Zn is added to form a solid solution with Mg and to enhance strength and elongation of the alloy. Where the amount of Zn is less than 0.95%, intended effect cannot be obtained. The amount of Zn more than 2.00% may be unpreferable, since Zn content may exceed the solid-solubility limit, resulting in non-desired formation of Zn-rich precipitates that reduce the corrosion resistance. Accordingly, the contained amount of Zn is set to 0.95% or more and 20.00% or less in the preferred magnesium alloy. However, the contained amount of Zn may be less than 2.00%

Zirconium (Zr): In % by Mass, 0.05% or More and Less than 0.03%

Zr scarcely forms solid-solution with Mg, and forms fine-grained precipitates, thereby preventing coarsening of crystal grains of alloys. Where the amount of Zr is less than 0.05%, effects of Zr addition cannot be obtained. Where the amount of Zr is 0.30% or more, precipitates may be formed in a higher amount, thereby may reduce the effect on particle size refinement. In addition, corrosion and breakage would start occurring at portions where the precipitates are biased. For this reason, content of Zr is regulated to 0.05% or more and less than 0.30% in the preferred magnesium alloy. The content of Zr may be 0.10% or more and less than 0.30%.

Manganese (Mn): In % by Mass, 0.05% or More and 0.20% or Less

Mn has effects of refining grain size of the alloy and enhancing corrosion resistance of the alloy. Where the amount of Mn is less than 0.05%, intended effects cannot be obtained. Where the amount of Mn is over 0.20%, workability in plastic working may be degraded. Accordingly, the contained amount of Mn is set to 0.05% or more and 0.20% or less in the preferred magnesium alloy. The preferable contained amount of Mn is 0.10% or more and 0.20% or less.

Unavoidable Impurities

For the medical magnesium alloy, it is preferable that the contained amount of the unavoidable impurities is also controlled. Since Fe, Ni, Co, and Cu enhance corrosion of the magnesium alloy, it is preferable to control an amount of each of these elements to be less than 10 ppm, more preferably 5 ppm or less, and still more preferably the magnesium alloy is essentially free of these elements. Preferably, the total amount of unavoidable impurities is controlled to be 30 ppm or less, more preferably 10 ppm or less. Further, it is preferable that the magnesium alloy is essentially free of rare earth and aluminum. Here, a state where the contained amount of a target substance is less than 1 ppm is recognized as "essentially free" of that substance. The amount of unavoidable impurities may be determined, for example, by ICP emission spectrometry.

Production of Magnesium Alloy

The above magnesium alloy can be produced, in accordance with usual production method of magnesium alloys, throwing ground metals or alloys of Mg, Zn, Zr, and Mn into a crucible, melting the ground metals and/or alloys in the crucible at a temperature of 650 to 800° C. to form a molten alloy, and casting the molting alloy. Where necessary, the cast alloy is subjected to solution heat treatment. Rare earth element-free (and aluminum-free) metals are used as the ground metals. It is possible to suppress the amounts of Fe, Ni, Co, and Cu in the impurities by the use of ground metals with high purity. Fe, Ni, and Co in the impurities of molten alloy may be removed by iron-extraction treatment after it has been melted. In addition or alternatively, it is possible to use ground metals produced by distillation refining.

Metallic Morphology and Mechanical Property

The magnesium alloy may have, in terms of grain size distribution, a fine and uniform structure having an average crystal grain size of 1.0 to 3.0 μm (for example, 1.0 to 2.0 μm), and a standard deviation of 0.7 or less (for example, 0.5 to 0.7), by means of controlling the composition of the alloy and controlling the method for manufacturing. The standard deviation is preferably 0.65 μm or less. The fine precipitate including Zr may have a grain size of less than 500 nm, preferably less than 100 nm. The matrix excluding the Zr precipitates is preferably a total solid solution of the Mg—Zn—Mn ternary alloy.

The alloy may have mechanical properties, as measured in accordance with JIS 2241, such as a tensile strength of 230 to 380 MPa (for example, 250 to 300 MPa), a proof strength of 145 to 220 MPa, and fracture elongation of 15 to 50% (for example, 25 to 40%). Here, the tensile strength preferably exceeds 280 MPa. The fracture elongation preferably exceeds 30%.

Shape of Magnesium Alloy

The magnesium alloy may have a wheel shape, a plate shape, a rod shape, a pipe shape, a band shape, a wire shape, a ring shape, or a combination of at least one shape as described above. On the magnesium alloy having a shape selected in view of its use, the above-described first layer and second layer may be formed.

Formation of Magnesium Fluoride Layer

The surface of the magnesium alloy (core structure) having a predetermined shape is subjected to fluorination treatment. As far as a $MgF_2$ layer can be formed, the conditions for fluorination treatment are not specifically limited. For example, the magnesium alloy can be immersed into a treating solution, such as a hydrofluoric-acid aqueous solution. It is preferred to immerse the magnesium alloy with shake, for example, at 50 to 200 ppm, preferably 80 to 150 ppm. Then, the magnesium alloy on which $MgF_2$ layer is formed is taken out of the solution, followed by washing sufficiently with cleaning fluid (for example, acetone aqueous solution), for example, by ultrasonic cleaning. Where the washed magnesium alloy is subjected to drying, it is preferred that the magnesium alloy is dried at 50 to 60° C. for 24 hours or longer under vacuum.

Structure of Magnesium Fluoride Layer

The magnesium fluoride layer comprises mainly magnesium fluoride. For example, magnesium fluoride layer may comprise mainly $MgF_2$ in a concentration of 90% or more. Further, oxides such as MgO and $Mg(OH)_2$ and hydroxides may be contained as auxiliary components. It should be noted that the magnesium fluoride layer may contain oxides and hydroxides of metals other than magnesium that constitute the medical device for above purpose.

Layer Thickness of Magnesium Fluoride Layer

The layer thickness of the magnesium fluoride layer may be preferably 0.5 μm or more in view of anticorrosion properties, and 1.5 μm or less in view of deformation followability.

Formation of Diamond-Like Carbon Layer

The diamond-like carbon coating layer can be formed using a chemical vapor deposition (CVD) method.

Figure 3:
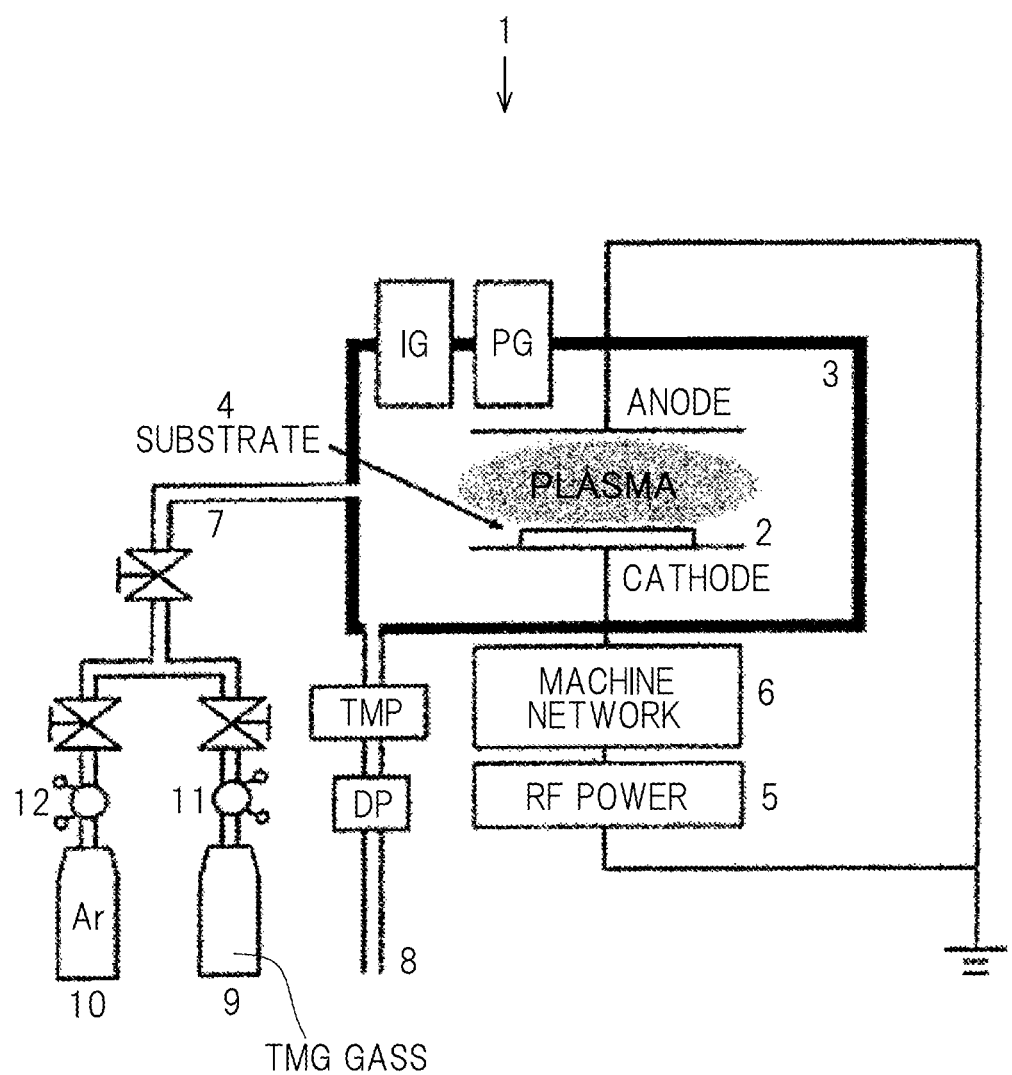
FIG. 3 is a schematic sectional view illustrating an example of the diamond-like carbon layer forming apparatus.

FIG. 3 is a schematic cross-sectional view of an apparatus used for forming a diamond-like carbon layer, and shows a plasma CVD apparatus comprising a high frequency power source as discharge power source. The plasma CVD apparatus 1 is provided with a vacuum vessel 3 in which an electrode plate 2 that also serves as a substrate holder is installed at a lower portion. On the electrode plate 2 a magnesium alloy (base substrate) 4 coated with a magnesium fluoride layer is placed. The electrode plate 2 is connected to a radio frequency (RF) power supply 5 and a blocking capacitor 6.

The vacuum vessel 3 is provided with a gas-introducing line 7 and a gas-exhausting port 8. The gas-introducing line 7 introduces a gas containing a carbon-containing gas (C-based gas such as methane gas, acetylene gas) or a silicon- and carbon-containing gas [Si—C-based gas such as tetramethlsilane (TMS)], which is a source gas, and a bombard treatment gas (an inert gas such as Ar). The gas-exhausting port 8 is connected to an exhaust system (not shown). The gas-introducing line 7 is connected to a source gas supply device 9 and a bombard gas supply device 10 via mass flow controllers 11 and 12, respectively. The vacuum vessel 3 is grounded.

The magnesium alloy 4 coated with the magnesium fluoride layer is placed on the electrode plate 2, then the pressure inside of the vacuum vessel 3 is adjusted to a predetermined pressure by exhausting gas from the gas-exhausting port 8 using a gas-exhausting system (not shown). A C-based gas (for example, acetylene) or a Si—C-based gas (for example, tetramethylsilane), which is a source gas (raw material gas), is supplied from a source gas supply device 9, and the flow rate is adjusted using a mass flow controller 11 so as to be introduced into the vacuum vessel 3. During this time, high frequency (RF) is applied from the high frequency power source 5 to the electrode plate 2 to make the C-based gas or Si—C-based gas introduced into the vacuum vessel 3 into the plasma CVD apparatus.

By applying self-bias to the electrode plate 2 on which the magnesium alloy 4 coated with the magnesium fluoride layer is placed, positive ions in the plasma apparatus are attached to the magnesium alloy 4, so that a dense diamond-like carbon thin film or a dense silicon-containing diamond-like thin film is locally formed on the surface of the magnesium fluoride layer of the magnesium alloy 4.

Specifically, a C-based gas containing carbon or a Si—C-based gas containing silicon and carbon used as a source gas is introduced into the chamber on which the base substrate is placed at a flow rate of 50 to 250 $cm^3$/min (1 atm, 0° C.), preferably 100 to 200 sccm, so as to give a pressure of 1 to 5 Pa, and a high frequency power of 100 to 500 W is applied to the RF electrode. Accordingly, a diamond-like carbon coat layer (DLC layer) or a silicon-containing diamond-like carbon coat layer (Si-DLC layer) is preferably formed.

Examples of the C-based gas containing carbon may include methane, ethane, propane, ethylene, propylene, acetylene, benzene, and the like, as main components. Alternatively, examples of the Si—C-based gas containing silicon and carbon may include monomethylsilane, triethylsilane, tetramethylsilane, and the like, as main components. Among them, tetramethylsilane and the like are preferably used.

In the case of forming a silicon-containing diamond-like carbon coating layer, a mixture of one or more silicon-based gases containing at least silicon and one or more carbon gases (such as alkanes) containing at least carbon may be used as the source gas.

Accordingly, the C-based gas (for example, acetylene) or the Si—C-based gas (for example, tetramethylsilane), as the source gas, is ionized by the plasma CVD method so as to form a DLC film on the surface of the magnesium fluoride layer on the magnesium alloy 4, resulting in a surface-modified magnesium alloy in which a DLC layer is formed on the magnesium fluoride layer.

Composition and Layer Thickness of the Diamond-Like Carbon (DLC) Layer

According to the present invention, by forming a thin DLC layer with a thickness of 10 nm to 5 μm on the magnesium fluoride layer, the corrosion resistance of the magnesium alloy can be greatly improved without interfering with its bioabsorbability. Where the thickness of the DLC layer is too thin, the corrosion protection effect tends to be insufficient, while the thickness of the DLC layer is too thick, the bioabsorbability tends to be interfered.

Biodegradable Resin Layer

According to the present invention, a biodegradable polymer layer may be formed on the entire surface or a part of the surface of the DLC layer. Examples of the biodegradable polymers may include polyesters, such as a poly-L-lactic acid (PLLA), a poly-D,L-lactic acid (PDLLA), a poly(lactic acid-glycolic acid) (PLGA), a polyglycolic acid (PGA), a polycaprolactone (PCL), a polylactic acid-ε-caprolactone (PLCL), a poly(glycolic acid-ε-caprolactone) (PGCL), a poly-p-dioxanone, a poly(glycolic acid-trimethylene carbonate), a poly-β-hydroxybutyric acid, and others.

Pharmaceutical (Drug)

Depending on the therapeutic purpose for which the surface-modified magnesium alloy according to the present invention is used, the biodegradable resin layer may contain a pharmaceutical (drug).

Medical Use

The obtained surface-modified magnesium alloy can be utilized in patient treatment as an alloy for orthopedic implants, an alloy for oral surgery implants, an alloy for plastic surgery implants, an alloy for cardiovascular surgery implants, an alloy for a lower limb stents, or an alloy for cerebral surgery implants. Specific examples may include alloys for suture instruments such as staplers, and surgical needles, and bone junction members such as bone pins, and bone screws, and therapeutic implants for luminal region, including gastrointestinal and esophageal implants, and other therapeutic implants such as for aneurysm coils.

Preparation of Magnesium Alloy

High purity ground metals of Mg, Zn, Mn, and Zr were prepared as initial materials. Each of the metals was weighed so as to have a component concentration as described in Table 1 and was thrown into a crucible. Then, at 730° C. the metals were molten with stirring, and a thus-obtained melt was cast to form ingots. Thus-obtained magnesium alloys of Production Example 1 and Production Example 2 contained the main components at formulation ratios which fall within the present invention. The initial materials used did not contain rare earth elements and aluminum even as unavoidable impurities. In this regard, 99.99% pure magnesium ground metal having a low concentration of impurity Cu was used. De-ironing treatment was carried out in the furnace in order to remove iron and nickel from the melt. Concentrations of impurities in the thus-obtained samples were determined using an ICP optical emission spectrometer (AGILENT 720 ICP-OES manufactured by AGILENT). Table 1 shows the compositions of Example 1 and Example 2. The concentrations of Fe, Ni, and Cu were all 8 ppm or lower (Ni and Cu were 3 ppm or lower). Al and the rare-earth elements were not detected, and Co was also below a detection limit. The total content of the unavoidable impurities 11 ppm.

TABLE 1

| | Component concentration (% by mass) | | | | Impurity concentration (ppm) | | | |
|---|---|---|---|---|---|---|---|---|
| | Mg | Zn | Mn | Zr | Fe | Ni | Cu | Total |
| Production Example 1 | the balance | 1.86 | 0.14 | 0.12 | 5 | 3 | 3 | 11 |
| Production Example 2 | the balance | 0.95 | 0.11 | 0.24 | 8 | 3 | 1 | 12 |

Measurement of Mechanical Properties

Each alloy according to the examples was formed into a round bar material through hot extrusion. In accordance with JIS Z2241, a tensile strength, a proof strength, and a fracture elongation of the round bar material were determined. Table 2 shows the results.

TABLE 2

| | Tensile strength (MPa) | Proof stress (MPa) | Fracture elongation (%) | Average grain size (μm) | Standard Deviation (μm) |
|---|---|---|---|---|---|
| Production Example 1 | 288 | 213 | 38 | 1.97 | 0.62 |
| Production Example 2 | 297 | 217 | 27 | 1.97 | 0.63 |

Mg Alloy Production Example 3

High purity ground metals of Mg, Zn, Mn, and Zr were prepared as raw materials. Respective components were weighted so as to constitute the component concentration shown below, and were thrown into a crucible, and were molten at 730° C. Each melt was stirred in the crucible, and was cast to form an ingot. Rare earth elements and aluminum were not contained in the raw materials even as unavoidable impurities.

Magnesium was provided from a magnesium ground metal of purity level of 99.99% with low concentration of impurity Cu, and molten alloys in the crucible were subjected to iron-extraction treatment so as to remove iron and nickel from the molten alloys.

Impurity concentrations of the thus obtained samples were measured using an ICP emission spectrometer (AGILENT 720 ICP-OES made by Agilent Technologies).

Component concentration (w %) of the obtained ingot was as follows, and the ingot did not contain aluminum and rare earths.

Mg Remnant, Zn 1.5%, Mn 0.4%, Zr 0.4%,

The ingot contained Fe, Ni, Co and Cu as unavoidable impurities at the following concentrations.

Fe 5 ppm, Ni 5 ppm, Co ND (below detection limits), Cu 1 ppm

Production of Magnesium Plate

Figure 2:
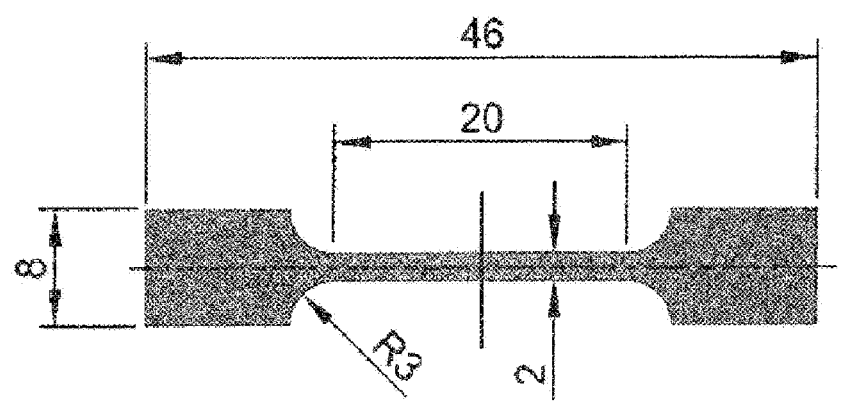
FIG. 2 is a schematic view illustrating an example of a surface-modified magnesium alloy implant according to an embodiment of the present invention.

The magnesium alloy ingot produced by Production Example 3 was processed into the shape (thickness: 1 mm) shown in FIG. 2 (the dimension shown in FIG. 2 is mm) so as to form a magnesium alloy substrate A.

The magnesium alloy ingot produced by Production Example 3 was also processed into a disc shape (diameter 50 mm×thickness 1 mm) so as to form a magnesium alloy substrate B.

Electrolytic Polishing of Magnesium Alloy Substrate

Oxide particles deposited on the surface of the obtained magnesium alloy substrate was removed by acid solution. The magnesium alloy substrate was then immersed in the electrolytic solution as a positive electrode, with placing metal plates as negative electrode, and these electrodes were electrically connected through a direct-current power supply. In such a state, a voltage was applied, whereby the magnesium alloy substrate of the positive electrode was mirror polished so as to obtain a smooth surface. In order to stabilize the mucous layer while applying the voltage, the electrolytic solution was agitated. In such a manner, the temperature was kept constant. Moreover, in order to suppress generation of air bubbles on the negative electrode, applying and cutting of the voltage was appropriately repeated. If the air bubbles are liberated from the negative electrode and deposited on the magnesium alloy substrate, defect on surface accuracy will arise.

From the obtained magnesium alloy substrate with the mirror-surface, the samples illustrated in the following Examples and Comparative Examples were prepared.

Evaluation of Weight Residual Ratio and Tensile Strength Residual Ratio Each of the obtained samples was immersed in the simulated plasma solution (EMEM+10% FBS), and was shaken at 100 rpm with keeping immersion at 37° C. under 5% $CO_2$ atmosphere. After 28 days of immersion, the sample was taken out of the solution and ultrasonically cleaned with chromic acid so as to completely remove corrosion products such as magnesium hydroxide, and the weight residual ratio before and after immersion was evaluated (n=5).

On another front, the obtained sample was shaken with keeping immersion in the same manner, and after 28 days of immersion, the sample was taken out of the solution and cleaned so as to remove corrosion products, and the sample was chucked in a tensile tester and subjected to a tensile test at a crosshead speed of 5 mm/min. In such a manner, the tensile strength residual ratio before and after immersion was evaluated (n=5).

Example 1

The magnesium alloy substrate A with the mirror surface was immersed in a 27M aqueous hydrofluoric acid solution and shaken at 100 rpm. The sample taken out of the solution after 24 hours was thoroughly ultrasonically cleaned with water and acetone, and then dried at 60° C. under reduced pressure for 24 hours. Accordingly, a sample having a magnesium fluoride layer (thickness 1 μm) was obtained. A diamond-like carbon layer with a thickness of 1 μm was further formed on the sample by CVD method so as to obtain a sample having a diamond-like carbon layer on a magnesium fluoride layer.

Example 2

A sample obtained in the same manner as in Example 1 was immersed in a 1% polylactic acid solution for 3 minutes. The 1% polylactic acid solution was prepared by dissolving 1% polylactic acid in THF. The sample taken out of the solution was dried at 60° C. under reduced pressure for 24 hours. In such a manner, a sample having a magnesium fluoride layer, a diamond-like carbon layer, and a polylactic acid layer in this order was obtained.

Comparative Example 1

The magnesium alloy substrate A with the mirror surface was immersed in a 27M aqueous hydrofluoric acid solution and shaken at 100 rpm. The sample taken out of the solution after 24 hours of immersion was thoroughly ultrasonically cleaned with water and acetone, and then dried at 60° C. under reduced pressure for 24 hours. Accordingly, a sample having a magnesium fluoride layer (thickness 1 μm) was obtained.

Comparative Example 2

The magnesium alloy substrate A with the mirror surface (unfluorinated) was subjected to CVD method so as to obtain a sample having a diamond-like carbon layer at a thickness of 1 μm.

Comparative Example 3

A sample obtained in the same manner as in Comparative Example 2 was immersed in a 1% polylactic acid solution for 3 minutes. The 1% polylactic acid solution was prepared by dissolving 1% polylactic acid in THF. The sample taken out of the solution was dried at 60° C. under reduced pressure for 24 hours. In such a manner, a sample having a polylactic acid layer on a diamond-like carbon layer was obtained.

Table 3 shows the results of measuring the weight residual ratio of the samples, Table 4 shows the results of measuring the tensile strength residual ratio of the samples. It should be noted that the weight of the sample before immersion was 0.36 f 0.1 g, and the tensile strength of the sample before immersion was 310 f 10 MPa.

TABLE 3

Weight residual ratio (%) before and after immersion

| | Before immersion | After immersion |
|---|---|---|
| Example 1 | 100 | 98.8 ± 0.6 |
| Example 2 | 100 | 97.9 ± 0.8 |
| Comparative Example 1 | 100 | 94.8 ± 1.2 |
| Comparative Example 2 | 100 | 86.5 ± 3.1 |
| Comparative Example 3 | 100 | 88.1 ± 4.3 |

TABLE 4

Tensile strength residual ratio (%) before and afterimmersion

| | Before immersion | After immersion |
|---|---|---|
| Example 1 | 100 | 95.0 ± 1.9 |
| Example 2 | 100 | 94.8 ± 1.2 |
| Comparative Example 1 | 100 | 87.8 ± 2.9 |
| Comparative Example 2 | 100 | 79.9 ± 3.8 |
| Comparative Example 3 | 100 | 78.7 ± 4.1 |

The samples according to the present invention (Example 1 and Example 2) had significantly smaller changes in weight and tensile strength compared to the sample without the diamond-like carbon layer (Comparative Example 1) and the samples without the magnesium fluoride layer (Comparative Examples 2 and 3), suggesting that an excellent anticorrosion effect can be obtained by the double layer structure of the magnesium fluoride layer and the diamond-like carbon layer.

Inflammatory Evaluation Caused by Placement of Implant Under Mouse Skin

A sample having excellent anticorrosive properties can suppress an inflammatory reaction related to corrosion in a living tissue. Accordingly, the anticorrosion property of the sample can be comprehended by means of evaluating the inflammation of the tissue.

The obtained test samples were implanted subcutaneously (under the skin) in the back of the mouse (two test samples per mouse), and on the $60^{th}$ day, the inflammation of the tissue was evaluated in accordance with the following 4 scores (n=5).

| Class | Criteria for evaluation |
|---|---|
| 0 | Inflammatory cells are not detected around the strut. |
| 1 | A few inflammatory cells were detected around the strut. |
| 2 | Inflammatory cells were detected at a covering amount of 50% or more in the area around the strut. |
| 3 | Entire surroundings of the strut was covered by inflammatory cells. |

Example 3

The magnesium alloy substrate B with the mirror surface was immersed in a 27M aqueous hydrofluoric acid solution and shaken at 100 rpm. The sample taken out of the solution after 24 hours was thoroughly ultrasonically cleaned with water and acetone, and then dried at 60° C. under reduced pressure for 24 hours. Accordingly, a sample having a magnesium fluoride layer (thickness 1 μm) was obtained. A diamond-like carbon layer C with a thickness of 1 μm was further formed on the sample by CVD method so as to obtain a sample having a diamond-like carbon layer on a magnesium fluoride layer.

Example 4

A sample obtained in the same manner as in Example 3 was immersed in a 1% polylactic acid solution for 3 minutes. The 1% polylactic acid solution was prepared by dissolving 1% polylactic acid in THF. The sample taken out of the solution was dried at 60° C. under reduced pressure for 24 hours. In such a manner, a sample having a polylactic acid layer on a diamond-like carbon layer on a magnesium fluoride layer was obtained.

Comparative Example 4

The magnesium alloy substrate B with the mirror surface was immersed in a 27M aqueous hydrofluoric acid solution and shaken at 100 rpm. The sample taken out of the solution after 24 hours was thoroughly ultrasonically cleaned with water and acetone, and then dried at 60° C. under reduced pressure for 24 hours. In such a manner, a sample having a magnesium fluoride layer (thickness 1 µm) was obtained.

Comparative Example 5

The magnesium alloy substrate B with the mirror surface (unfluorinated) was treated by the CVD method so as to obtain a sample having a diamond-like carbon layer in a thickness of 1 µm.

Comparative Example 6

A sample obtained in the same manner as in Comparative Example was immersed in a 1% polylactic acid solution for 3 minutes. The 1% polylactic acid solution was prepared by dissolving 1% polylactic acid in THF. The sample taken out of the solution was dried at 60° C. under reduced pressure for 24 hours. In such a manner, a sample having a polylactic acid layer on a diamond-like carbon layer was obtained.

Inflammatory evaluations of the samples obtained in Examples 3, 4 and Comparative Examples 4 to 6 were illustrated in Table 5.

TABLE 5

Inflammatory score of mouse at 60 day after subcutaneous implant.

|  | No. 1 | No. 2 | No. 3 | No. 4 | No. 5 | Average |
|---|---|---|---|---|---|---|
| Example 3 | 1 | 1 | 1 | 1 | 1 | 1.0 ± 0.0 |
| Example 4 | 1 | 1 | 1 | 1 | 1 | 1.0 ± 0.0 |
| Com. Ex. 4 | 1 | 2 | 2 | 2 | 2 | 1.8 ± 0.4 |
| Com. Ex. 5 | 2 | 2 | 2 | 2 | 1 | 1.8 ± 0.4 |
| Com. Ex. 6 | 2 | 2 | 2 | 2 | 2 | 2.0 ± 0.0 |

Note:
No. 1 to No. 5 indicate Sample No.

The samples according to the present invention (Example 3 and Example 4) showed significantly smaller inflammatory scores of the tissues compared to the sample without the diamond-like carbon layer (Comparative Example 4) and the samples without the magnesium fluoride layer (Comparative Examples 5 and 6), suggesting that an excellent anticorrosion effect can be obtained by the double layer structure of the magnesium fluoride layer and the diamond-like carbon layer.

INDUSTRIAL APPLICABILITY

The present invention provides a surface-modified magnesium alloy including: a magnesium fluoride layer effective in delaying the decrease in mechanical strength associated with accelerated corrosion of the magnesium alloy structure; and a diamond-like carbon layer formed on the magnesium fluoride layer. Since such an alloy can contribute to the development on medical technology, it has extremely high industrial potential.

Although the present invention has been fully described in connection with the preferred examples thereof with reference to the accompanying drawings, those skilled in the art can easily assume various changes and modifications within a self-evident range by looking at the present specification and the drawings. Accordingly, such changes and modifications are to be construed as being within the scope of the invention from the claims.

REFERENCE NUMERALS a . . . Mg alloy
b . . . First covering layer (magnesium fluoride layer)
c . . . Second covering layer (diamond-like carbon layer)
1 . . . Diamond-like carbon layer forming device
2 . . . Electrode plate
3 . . . Vacuum vessel
4 . . . Substrate (magnesium alloy on which a magnesium fluoride layer is formed)
5 . . . High-frequency (RF) power source
6 . . . Blocking capacitor
7 . . . Gas-introducing line
8 . . . Gas-exhausting port
9 . . . Source gas supply device
10 . . . Bombard gas supply device
11 . . . Mass flow controller
12 . . . Mass flow controller

What is claimed is:

1. A surface-modified magnesium alloy comprising:
a magnesium alloy having an arbitrary shape;
a magnesium fluoride layer formed on the magnesium alloy via fluorination of a surface of the magnesium alloy; and
a diamond-like carbon layer formed on the magnesium fluoride layer, wherein the magnesium alloy contains, in % by mass, 0.95 to 2.00% Zn, 0.05% or more and less than 0.30% Zr, 0.05 to 0.20% Mn, and the balance consisting of Mg and unavoidable impurities, with an average crystal grain size of 1.0 to 3.0 µm and a standard deviation of grain size distribution of 0.7 or less.

2. The surface-modified magnesium alloy according to claim 1, wherein the magnesium alloy has a wheel shape, a plate shape, a rod shape, a pipe shape, a band shape, a wire shape, a ring shape, or a combination of at least one shape as described above.

3. The surface-modified magnesium alloy according to claim 1, wherein the surface-modified magnesium alloy is an alloy used (1) as therapeutic implants for non-luminal region, including for suture instruments and for bone junction members or (2) as therapeutic implants for luminal region, including gastrointestinal and esophageal implants, and other therapeutic implants including circulatory stents, lower extremity stents, and aneurysm coils.

4. The surface-modified magnesium alloy according to claim 1, wherein the magnesium fluoride layer has a layer thickness of 0.5 to 1.5 µm.

5. The surface-modified magnesium alloy according to claim 1, wherein the diamond-like carbon layer has a layer thickness of 10 nm to 5 µm.

6. The surface-modified magnesium alloy according to claim 1, wherein the diamond-like carbon layer is a silicon-containing diamond-like carbon layer.

7. The surface-modified magnesium alloy according to claim 1, wherein a biodegradable polymer layer is formed on at least a part of the surface of the diamond-like carbon layer.

* * * * *